United States Patent
Schneider et al.

(10) Patent No.: US 9,572,696 B2
(45) Date of Patent: Feb. 21, 2017

(54) STENT LOADING AND DELIVERY DEVICE HAVING A LOADING BASKET LOCK MECHANISM

(71) Applicant: BOSTON SCIENTIFIC SCIMED, INC., Maple Grove, MN (US)

(72) Inventors: Eric M. Schneider, Cumberland, RI (US); Jeffrey V. Bean, Fitchburg, MA (US); Andrew Kendall Hollett, Somerville, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/994,985

(22) Filed: Jan. 13, 2016

(65) Prior Publication Data

US 2016/0128854 A1 May 12, 2016

Related U.S. Application Data

(63) Continuation of application No. 14/540,492, filed on Nov. 13, 2014, now Pat. No. 9,265,639, which is a (Continued)

(51) Int. Cl.
*A61F 2/06* (2013.01)
*A61F 2/95* (2013.01)
*A61F 2/966* (2013.01)

(52) U.S. Cl.
CPC ............... *A61F 2/95* (2013.01); *A61F 2/966* (2013.01); *A61F 2002/9505* (2013.01);
(Continued)

(58) Field of Classification Search
CPC .............. A61F 2/966; A61F 2002/9517; A61F 2002/9522; A61F 2002/9534; A61F 2002/9665; A61F 2250/009; A61F 2/95
See application file for complete search history.

(56) References Cited

U.S. PATENT DOCUMENTS 5,376,094 A 12/1994 Kline
5,575,694 A 11/1996 Hawkins et al.
(Continued)

OTHER PUBLICATIONS

Boston Scientific, "Endoscopy Product Listing", HTTP://WWW.BOSTONSCIENTIFIC.COM/templatedata/imports/collateral/Endoscopy/oth_gastrolist_01_us.pef, 2008 (1 pg).
(Continued)

*Primary Examiner* — Ashley Fishback
(74) *Attorney, Agent, or Firm* — Seager, Tufte & Wickhem, LLP

(57) ABSTRACT

A stent loading and delivery system, the delivery system comprising an inner elongate tubular member having a proximal end and a distal end, an intermediate elongate tubular member having a proximal end and a distal end in sliding relationship to said inner elongate tubular member and an external elongate tubular member having a proximal end and a distal end in sliding relationship to said intermediate elongate tubular member, said intermediate elongate tubular member comprising a stop mechanism at its proximal end, wherein the stop mechanism prevents the external elongate tubular member from being slid past the stop mechanism when the external elongate tubular member is slid in a proximal direction.

20 Claims, 5 Drawing Sheets

Related U.S. Application Data continuation of application No. 13/328,023, filed on Dec. 16, 2011, now abandoned.

(60) Provisional application No. 61/428,261, filed on Dec. 30, 2010.

(52) U.S. Cl.
CPC ............... *A61F 2002/9517* (2013.01); *A61F 2002/9522* (2013.01); *A61F 2002/9534* (2013.01); *A61F 2002/9665* (2013.01); *A61F 2250/009* (2013.01)

(56) References Cited

U.S. PATENT DOCUMENTS

| | | |
|---|---|---|
| 5,846,248 A | 12/1998 | Chu et al. |
| 6,007,546 A | 12/1999 | Snow et al. |
| 6,010,512 A | 1/2000 | Chu et al. |
| 6,050,995 A | 4/2000 | Durgin |
| 6,447,835 B1 | 9/2002 | Wang et al. |
| 6,517,539 B1 | 2/2003 | Smith et al. |
| 6,890,348 B2 | 5/2005 | Sydney et al. |
| 6,939,361 B1 | 9/2005 | Kleshinski |
| 2002/0161389 A1 | 10/2002 | Boyle et al. |
| 2003/0028235 A1 | 2/2003 | McIntosh et al. |
| 2006/0224227 A1 | 10/2006 | Chobotov |
| 2007/0270932 A1 | 11/2007 | Headley et al. |
| 2008/0109058 A1 | 5/2008 | Greenberg et al. |
| 2009/0082779 A1* | 3/2009 | Nakao .............. A61B 17/00234 606/114 |
| 2009/0192518 A1 | 7/2009 | Golden et al. |

OTHER PUBLICATIONS

Boston Scientific, "Captivor® II Snare", HTTP://WWW.BOSTONSCIENTIFIC.COM/Device.bsci?page=HCP_Over-view&navReiid=1000.1003&method=DevDetailHCP&id=10074592&pageDisclaimer=Disclaimer.ProductPage, Mar. 25, 2012 (1 pg).

\* cited by examiner

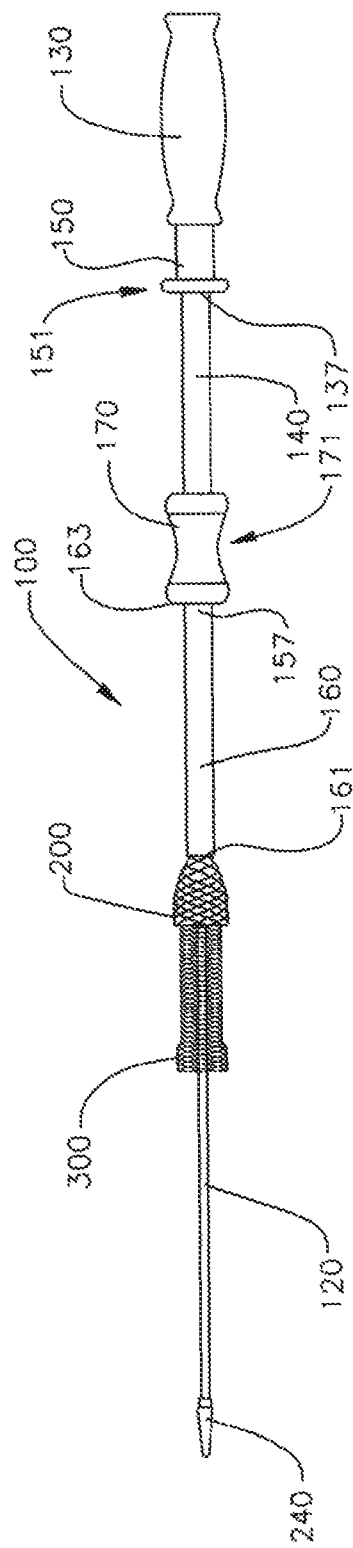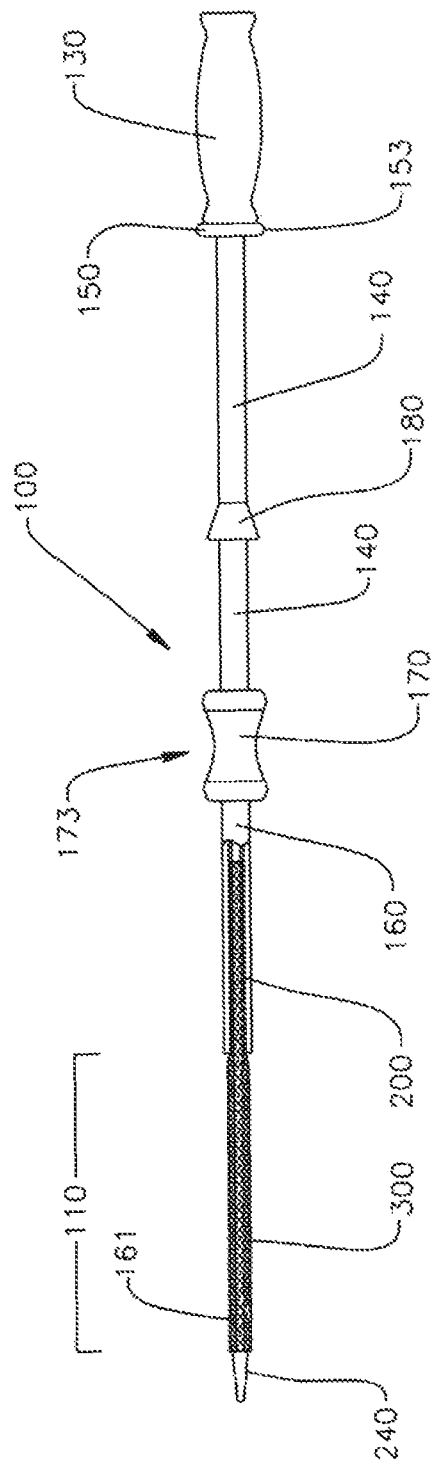

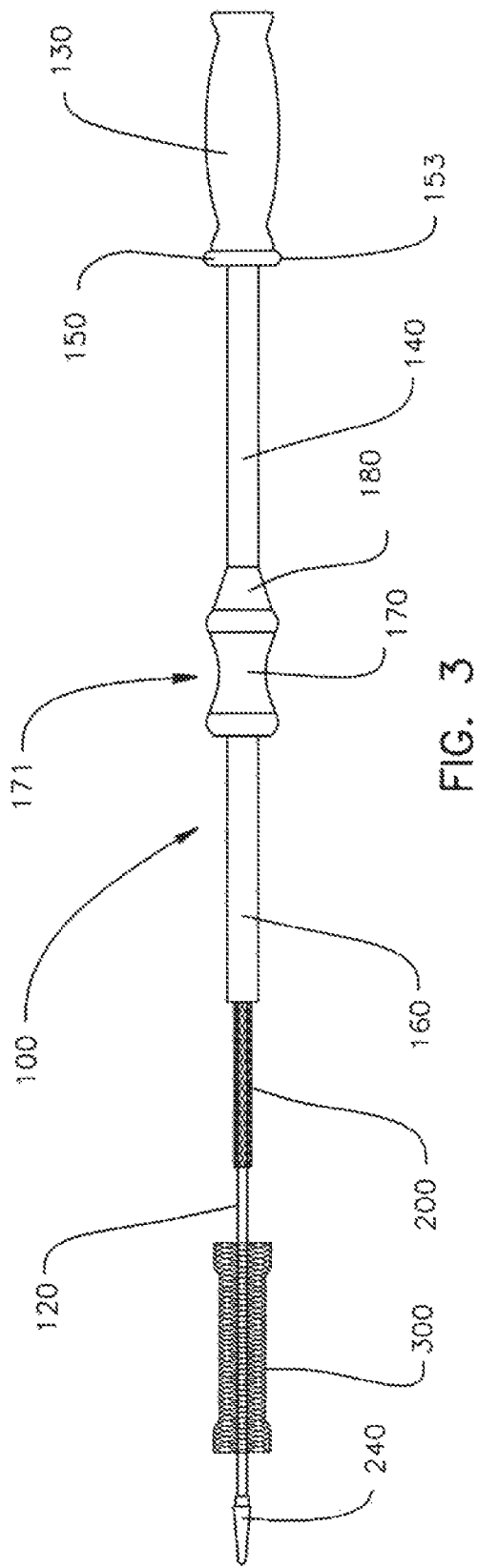
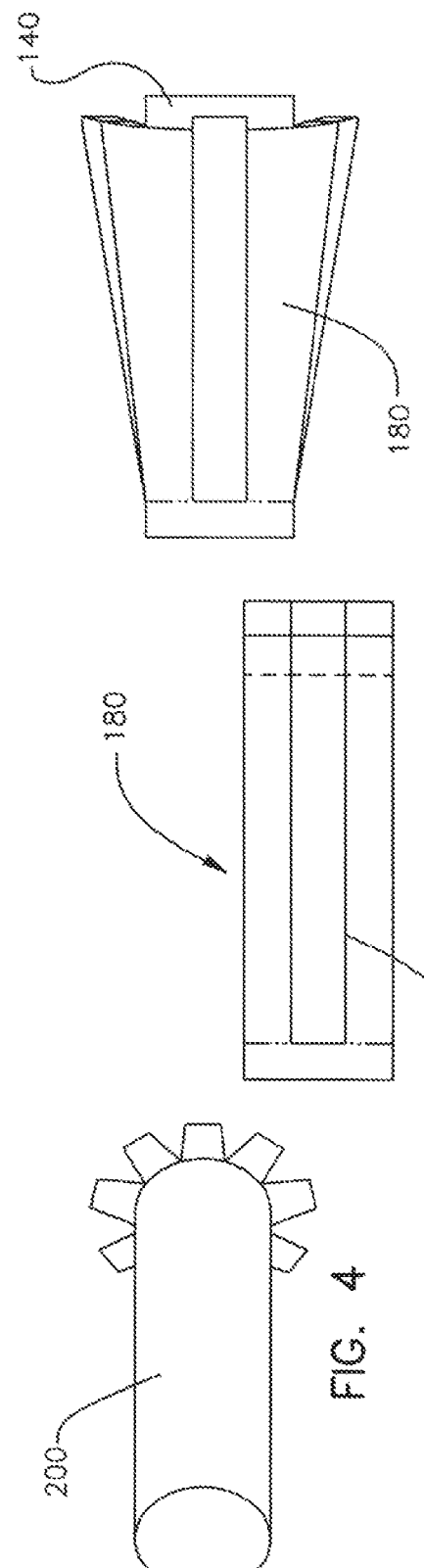
FIG. 3
FIG. 5A
FIG. 5B
FIG. 4

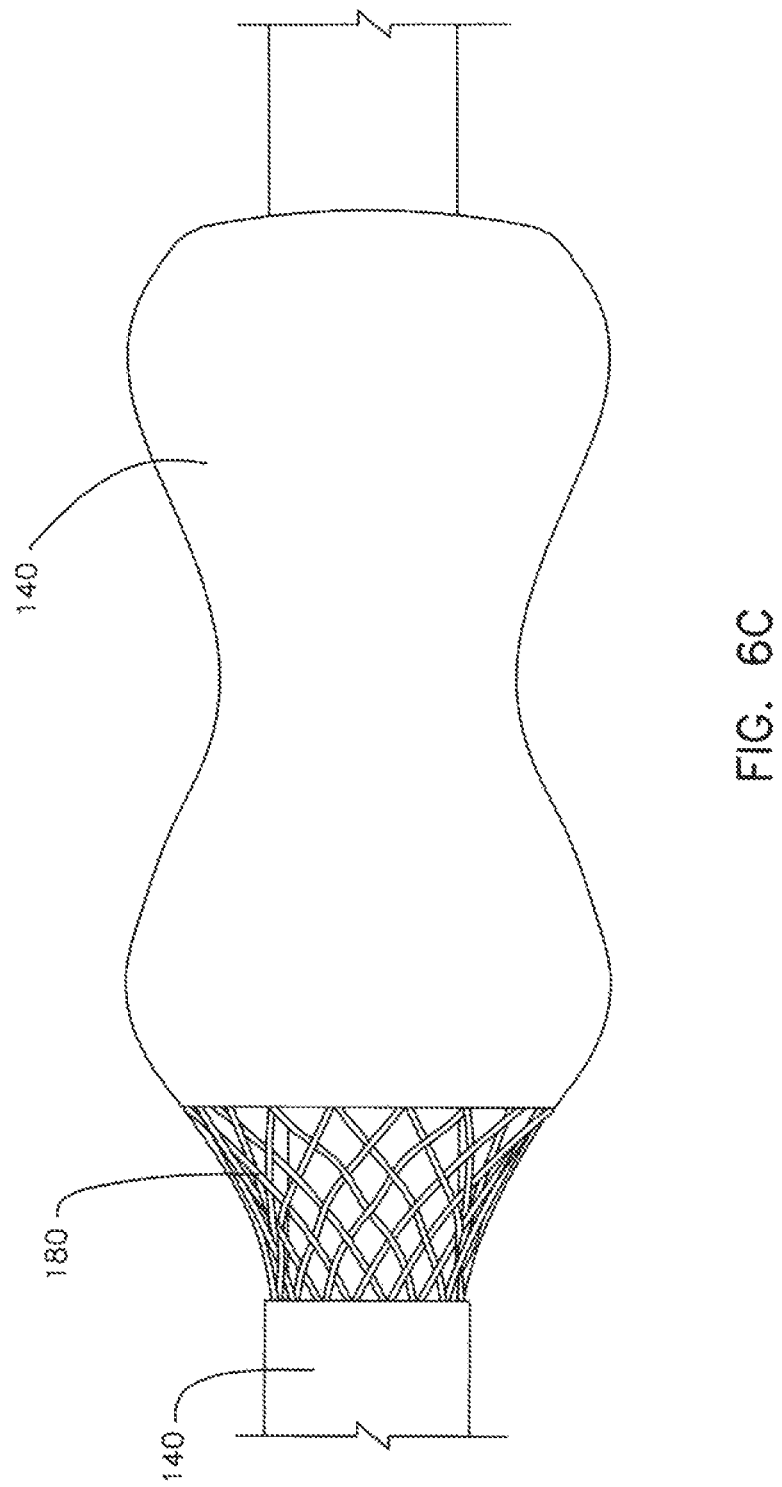

STENT LOADING AND DELIVERY DEVICE HAVING A LOADING BASKET LOCK MECHANISM

CROSS-REFERENCE TO RELATED APPLICATIONS

This application is a continuation of U.S. patent application Ser. No. 14/540,492, filed Nov. 13, 2014, which is a continuation of U.S. patent application Ser. No. 13/328,023, filed Dec. 16, 2011, which claims priority to U.S. Patent Provisional Application No. 61/428,261 filed Dec. 30, 2010, the entire contents of which are hereby incorporated herein by reference.

BACKGROUND OF THE INVENTION

The present invention relates to an assembly for loading and delivering a stent.

An intraluminary prosthesis is a medical device used in the repair and/or treatment of diseases in various body vessels, for example, a stent. Stents are generally cylindrical shaped devices that are radially expandable to hold open a segment of a blood vessel or other anatomical lumen after implantation into the body lumen. For example, stents may be used in the coronary or peripheral vasculature, esophagus, trachea, bronchi colon, biliary tract, urinary tract, prostate, brain, as well as in a variety of other applications in the body. These devices are implanted within the vessel to open and/or reinforce collapsing or partially occluded sections of the lumen.

Stents may be formed of metallic materials as well as polymeric and biodegradable materials, either in total or in part. In many procedures, polymeric or bioabsorbable prostheses are preferred over metallic devices, for example, due to the relative ease of removing a device intended for temporary implantation, or the capacity to be absorbed into the body.

When maintained in the reduced-radius state under a constant load for any appreciable length of time, a prosthesis formed of polymeric or bioabsorbable material may, however, undergo permanent or plastic deformation. When released from the catheter or other delivery device, such prosthesis may radially self expand to a diameter considerably less than its relaxed-state diameter prior to preloading. This phenomenon is commonly referred to as stress relaxation or "creep". This phenomenon is aggravated when a polymeric or bioabsorbable prosthesis is exposed to elevated temperatures in its reduced-radius state, for example during a sterilization procedure, which may be performed prior the outset of the prosthesis deployment procedure.

To counteract this phenomenon of stress relaxation or creep, the polymeric or bioabsorbable prosthesis may be sterilized and/or stored in its relaxed state, i.e., not significantly reduced radial state, until just before it is to be used. When the physician is about to begin a procedure, he or she may load the polymeric prosthesis into the delivery system. Consequently, the prosthesis remains compressed in the reduced-radius state only for a short time, perhaps only several minutes. While such a procedure counteracts the problem of creep, the procedure is, however, more difficult and time consuming. Although it is common practice to load a stent into a sheath during assembly of a stent delivery system, such loading often involves numerous steps and often requires the use of multiple components (e.g., tools and fixtures) that are not part of the stent delivery system. For example, currently available stent delivery systems often require that a stent be loaded onto a delivery system by means of a funnel, basket or other similar device which are not part of the delivery system.

There remains a need in the art for an improved stent loading device that is permanently attached to a stent delivery system to allow loading of a stent into stent delivery systems at the time of use, while minimizing the risk of damaging the stent in the process.

SUMMARY OF THE INVENTION

The present invention is directed to a method and system for delivering a self-expanding stent into a body lumen. In particular, the present invention relates to an assembly and a method for loading and delivering a stent in combination with a stent delivery catheter device, as well as to overall stent delivery systems.

In one embodiment, the present invention relates to a stent loading and delivery system, the delivery system including an inner elongate tubular member having a proximal end and a distal end, an intermediate elongate tubular member having a proximal end and a distal end in sliding relationship to said inner elongate tubular member and an external elongate tubular member having a proximal end and a distal end in sliding relationship to said intermediate elongate tubular member, said intermediate elongate tubular member comprising a stop mechanism at its proximal end, wherein the stop mechanism prevents the external elongate tubular member from being slid past the stop mechanism when the external elongate tubular member is slid in a proximal direction.

In one embodiment, the present invention relates to a stent loading and delivery system including an inner elongate tubular member having a proximal end and a distal end, the inner elongate tubular member having a proximal handle at the proximal end, an intermediate elongate tubular member in sliding relationship to the inner elongate tubular member, the intermediate elongate intermediate member having a proximal end and a distal end, the intermediate elongate tubular member having an intermediate handle, the intermediate handle having a first position and a second position, in the second position the intermediate handle is adjacent the proximal handle, an external elongate tubular member having a proximal end and a distal end, the external elongate tubular member overlying at least a portion of the intermediate elongate tubular member, the external elongate tubular member having a distal handle at the proximal end of the external elongate tubular member, the distal handle having a proximal position and a distal position and a stop mechanism secured to the proximal end of the elongate intermediate member at a point corresponding to the proximal position of the distal handle of the elongate external tubular member, the stop mechanism having a first unexpanded state and a second expanded state wherein when the distal handle of the external elongate tubular member is in the proximal position, the proximal end of the external elongate tubular member overlies the stop mechanism and the stop mechanism is in its unexpanded state and when the distal handle of the external elongate tubular member is in the second distal position the stop mechanism is exposed and is in its expanded state, the stop mechanism preventing the distal handle from moving to a point beyond the stop mechanism.

The device may further include a stent loading basket having opposed proximal and distal ends. In some embodiments, the proximal end may be securely disposed to the distal end of the intermediate elongate tubular member. The stent basket may have a truncated-conical shape, outwardly diverging in a distal direction from its proximal end. The stent basket may be a thin film which can collapse such that the stent basket may be slidably contained within the external member, or may be a radially distensible member which can collapse such that the stent basket may be slidably contained within the external member. In some embodiments, the stent basket may be composed of a polymeric material. The stent basket may include, in part or substantially, braided polymeric filaments. The braided filaments may be contained within a thin polymeric film. The intermediate member may be an elongate tubular device. The stent basket may comprise metals, polymers, or combinations of both.

In another embodiment, the present invention relates to A stent loading and delivery device including at least one inner tube having a proximal end and a distal end and a stop mechanism located at the proximal end and at least one outer tube having a proximal end and a distal end, the outer tube in sliding relationship with said at least one inner tube, the stop prevents the outer tube from advancing proximally when the proximal end of the outer tube is adjacent the stop.

The method of utilizing the system for stent loading and delivery is also contemplated herein.

These and other aspects, embodiments and advantages of the present disclosure will become immediately apparent to those of ordinary skill in the art upon review of the Detailed Description and Claims to follow.

BRIEF DESCRIPTION OF THE DRAWINGS

FIG. 1 is a side view of an embodiment of a stent loading and delivery device according to the invention prior to stent loading.

FIG. 2 is a side view of an embodiment of a stent loading and delivery device similar to that shown in FIG. 1 wherein the stent and stent loading basket have been loaded into the distal end of the external elongate tubular member.

FIG. 3 is a side view of an embodiment of a stent loading and delivery device similar to that shown in FIGS. 1 and 2 wherein the stent has been deployed and the stent loading basket remains in the distal end of the external elongate tubular member.

FIG. 4 is an embodiment of a stop mechanism according to the invention.

FIG. 5A is an alternative embodiment of a stop mechanism according to the invention prior to expansion.

FIG. 5B is an embodiment of a stop mechanism similar to that shown in FIG. 5A in an expanded state.

FIG. 6C is an embodiment of a stop mechanism similar to that shown in FIGS. 6A and 6B in an expanded state with the distal handle of the external elongate tubular member adjacent thereto.

DETAILED DESCRIPTION OF THE INVENTION

Figure 6A:
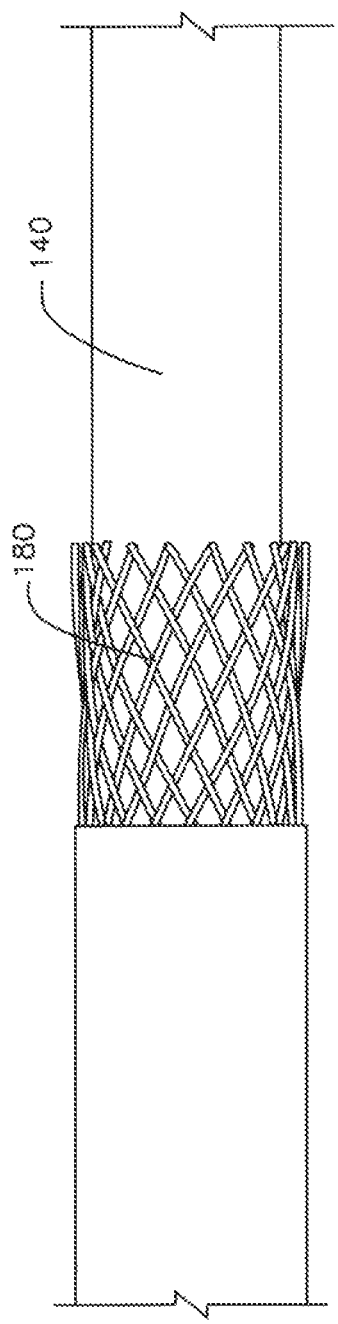
FIG. 6A is an alternative embodiment of a stop mechanism according to the invention in an unexpanded state.

While embodiments of the present disclosure may take many forms, there are described in detail herein specific embodiments of the present disclosure. This description is an exemplification of the principles of the present disclosure and is not intended to limit the disclosure to the particular embodiments illustrated.

As shown in the drawings and described throughout the following description, as is traditional when referring to relative positioning on an object, the term "proximal" refers to the end of the apparatus that is closer to the user and the term "distal" refers to the end of the apparatus that is further from the user. The distal end in the operative position is located within the patient's body and the proximal end in the operative position is located outside the patient's body.

The present application is directed to stent loading and delivery device including an inner elongate tubular member, an intermediate elongate tubular member having a stop mechanism located on its proximal end and an external elongate tubular member. The system may further include a stent loading basket wherein the proximal end of a stent is disposed and held therein in an expanded or non-contracted state. The stent loading basket and stent can be loaded into the external elongate tubular member between the external member and the inner elongate tubular member and is held adjacent to the loading basket but no longer disposed therein. When the stent is deployed using the external elongate tubular member, a stop mechanism incorporated with the intermediate elongate tubular member prevents the loading basket from being deployed from within the external elongate tubular member. The device will be described in detail with respect to the drawings below.

The method of utilizing the stent loading and delivery device is also contemplated by the present invention. In some embodiments, the utilization may include a method for loading, delivery and deployment of a stent utilizing the system in percutaneous, transluminal or other insertion techniques. The device allows the practitioner to easily load a stent into the delivery system with minimal effort and without damaging the stent.

Turning now to the figures, FIG. 1 is a cross-sectional view of a stent loading and delivery system 100 according to the present invention. The system 100, as depicted, may be particularly well suited for loading, transluminal delivery and intraluminal deployment of a radially self-expanding prosthesis, such as a stent and/or a stent-graft. The system 100 may include a catheter-type device with three elongated cylindrical members concentric about an axis and having opposed proximal and distal ends. The three members can be structured as follows: A flexible inner elongate tubular member 120, an intermediate elongate tubular member 140 slidably containing the inner member 120 therein, and an external elongate tubular member 160 slidably containing the intermediate member 140 therein.

Stent loading basket 200 is secured to the distal end of the intermediate member and lies adjacent the distal end of the external member and holds stent 300 in an unconstrained state therein.

Each member 120, 140, 160 of the system 100 may be controlled at the proximal end by a respective handle as follows. A proximal handle 130 may be fixedly disposed at the proximal end 117 of the inner member 120, handle 150 may be disposed at the proximal end 137 of the intermediate member 140 and handle 170 may be disposed at the proximal end 157 of the external member 160. Handle 170 is shown disposed furthest away from the practitioner in relation to other handles or away from the proximal end 117 of the inner member 120 in this embodiment. The intermediate handle 150 may be disposed between the distal handle 170 and the proximal handle 130, which may be disposed closest to the practitioner.

Handles 130, 150, and 170 are displaceable along the longitudinal axis 98 relative to each other thereby enabling selective deployment and retraction of the stent 300. Manipulation or axial movement of the handles 130, 150 and 170 permits independent axial movement of the tubular members 120, 140, and 160, respectively. For example, handle 150 may slide between a distal position 151 shown in FIG. 1 and a proximal position 153 shown in FIG. 2 so as to axially move the intermediate member 140. Such movement may be done while keeping the other handles 130, 170 fixed or relatively fixed to allow independent or substantially independent movement of the intermediate member 140. While the intermediate member 140 is moved, the inner member 120 and the external member 160 may remain fixed or relatively fixed.

Handle 170 is fixedly attached to the distal end 157 of external member 160 and moves proximally and distally between first and second positions 171 (proximal), 173 (distal).

When handle 170 is moved from proximal position 171 to distal position 173 stent loading basket 200 which engages and secures a proximal end of stent 300 is compressingly loaded along with stent 300 into the distal end 161 of the external tubular member 160 and holds the stent in a collapsed and constrained position over the inner tubular member 120 as shown in FIG. 2.

The intermediate handle 150 is moved from a distal position shown at 151 in FIG. 1 to a proximal position 153 adjacent handle 130 as shown in FIG. 2. This seats the stent 300 immediately adjacent stent loading basket 200 with the proximal end of the stent 300 no longer within loading basket 200 as shown in FIG. 2.

During the loading of the stent 300, the handles 170 and 150 may be kept fixed in relatively constant axial displacement from one and another. As such, the inner member 120 and the intermediate member 140 may also be kept in relative constant axial positions with the intermediate member 140 being substantially disposed within the external member 160. However, the intermediate member 140 need not be completely contained within the external member 160. Rather, a portion of the distal end of the intermediate member 140 may be axially outside or distally disposed from the distal end of the external member 160.

An added feature may be a stent holder (not shown) which can be provided on a distal portion referred to as the stent engagement region 110 of the inner elongate tubular member 120 to temporarily hold the stent in place without any substantial external force acting on it. The stent holder may be further defined by a tubular band (not shown). The stent holder may releasably hold stent 300 within system 100 even after the stent basket 200 may be axially displaced away from the stent 300. Such feature may allow, if desired, for a large portion of the stent 300 to be deployed and then be recaptured or re-engaged by stent basket 200 prior to complete deployment of the stent 300. The recapturing may be achieved by axially sliding the external member 160 over the stent 300. Moreover, the stent basket 200 may be repositioned between the inner member 120 and the external member 160, for example, by axially advancing the stent basket 200 to reposition the stent 300 therein between. Furthermore, the whole system 100 may be moved proximally or distally to reposition the stent 300 therein. These features may provide, among other things, reloading ability (reconstrainability) of the stent 300 within the system 100 of the present invention. These features are described more fully in US Patent Publication No. 2009/0192518.

Thus, during delivery through a patient's body lumen, the stent 300 is releasably secured in the stent deployment region 110 between the inner and outer tubular members 120, 160.

The stent delivery system 100 can now be positioned in the patient for deployment of stent 300. Insertion of the distal end of the system 100 into a patient's body is performed with a lead-in such as the distal end tip 240. Once the practitioner navigates the distal end tip 240 to a desired location, and is satisfied with the location and orientation of the partially deployed stent 300, the practitioner can actuate the handle 170 to its proximal position 171 to release fully deploy the stent 300 from the deployment region 110 of the delivery system as depicted in FIG. 3. The practitioner can then pull back the distal handle 170 toward the intermediate handle 150, thereby pulling back the external member 160. This step uncovers the constrained stent 300 can be unloaded at the desired deployment site. The delivery system 100 can then be removed from the body.

It should be noted that the stent loading and delivery device can be configured and arranged to allow a practitioner to re-load the stent in the event that it is positioned at the wrong location within a patient. For example, the intermediate handle 150 may have a release mechanism such that the intermediate handle 150 can be repositioned back to the original position if the stent 300 needs to be removed from the body and re-loaded. Optionally, the system can be positioned by axially moving or sliding the stent engaging basket 200 to a location past the stent deployment region 110 for disengagement of the stent 300 from the intermediate member 140.

A device of this type can be found in US Patent Publication No. 2009/0192518, the entire content of which is incorporated by reference herein.

A stop mechanism 180 is located at and secured to the proximal end of the intermediate member 140 which corresponds to position 171 of handle 170. When handle is at position 170 the external member 160 constrains the stop mechanism in a first collapsed position. As shown in FIGS. 2 and 3, when the handle 170 is moved distally to position 173 the stop mechanism expands to form a conical flare at one end. When the handle 170 is moved back to position 171 after stent deployment, the stop mechanism prevents the external member 160 from being retracted any further and deploying stent loading basket 200 from the distal end 161 of the external elongate tubular member. This prevents the catheter assembly from being reused for future procedures.

One embodiment of a stop mechanism 180 is shown in FIG. 4. In this embodiment, the distal end of the stop mechanism comprises flanges 210 which expand outwardly once the handle 170 is moved in a distal direction to position 173.

An alternative stop mechanism 180 is shown in FIG. 5A (unexpanded state) and FIG. 5B (expanded state). The stop mechanism 180 is shown in the shape of a frustoconical cone having tabs or pleats 190 formed therein.

Figure 6B:
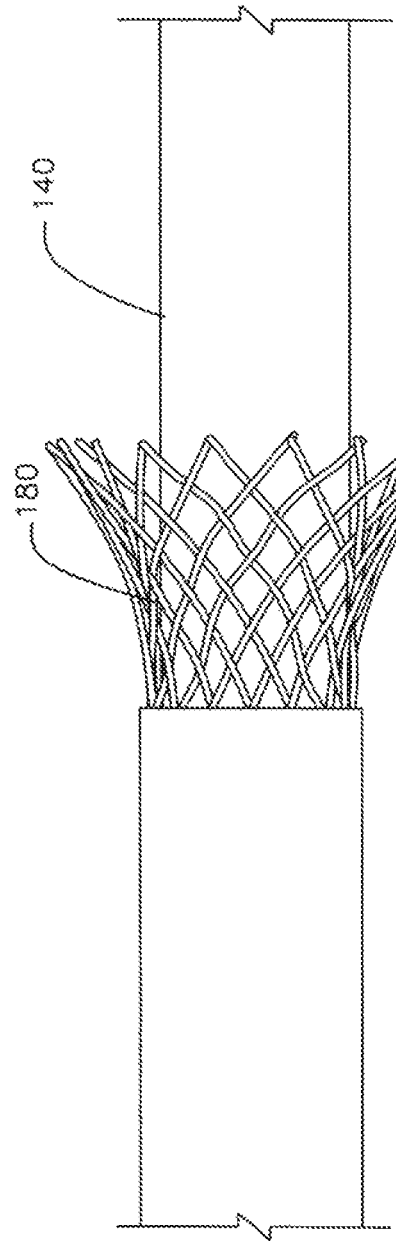
FIG. 6B is an embodiment of a stop mechanism similar to that shown in FIG. 6A in an expanded state.

Yet another alternative design can be found in FIG. 6A (unexpanded state), FIG. 6B (expanded state), and FIG. 6C (shown secured to the intermediate elongate tubular member 140 and adjacent to the distal handle 170 of the elongate external tubular member 160 when the distal handle 170 is in its proximal position again after stent deployment). This stops the external elongate tubular member 160 from being moved any further proximally and prevents the loading basket 200 from being deployed from within the distal end 161 of the elongate external tubular member 160 (also shown in FIG. 3). The stop mechanism 180 depicted in FIGS. 6A-6C is in the form of a tubular braid, much like a braided stent.

In any of the above embodiments, the tubular members 120, 140, and 160 may be formed of a biocompatible material such as a biocompatible polymer.

Examples of biocompatible polymers include, but are not limited to, polyolefins such as polyethylene (PE), high density polyethylene (HDPE) and polypropylene (PP), polyolefin copolymers and terpolymers, polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. Materials for the tubular members 120, 140, 160 may be same or different.

It should be noted that the stop mechanism 180, while shown as having a conical flare when expanded, can be anything that is covered by the external handle 160 upon loading, but is exposed when the handle 160 is moved distally. The form of the stop mechanism 180 may include, but is not limited to, a compressible bump, a raised portion on the intermediate member 140, a leaf spring, etc.

Figure 7:
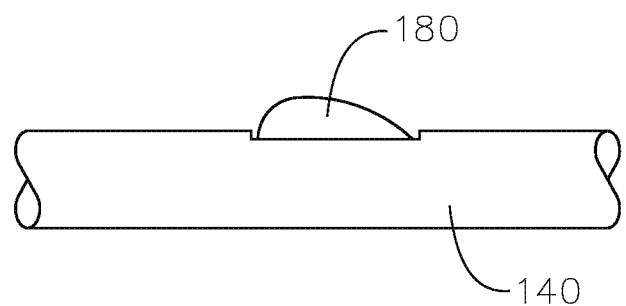
FIG. 7 is a partial view of an intermediate member showing an alternative embodiment of a stop mechanism in the form of a compressible bump.

FIG. 7 is a partial view of intermediate member 140 illustrating an alternative embodiment wherein the stop mechanism 180 is in the form of a compressible bump or sleeve on the intermediate member 140.

Figure 8A:
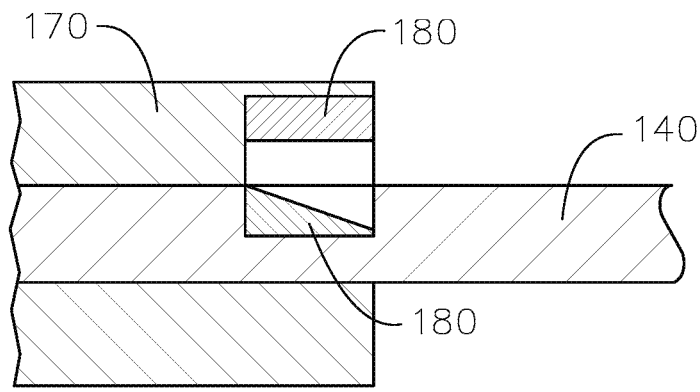
FIG. 8A is partial view of an intermediate member showing an alternative embodiment of a stop mechanism in an unexpanded state wherein stop mechanism is disposed on the intermediate member and in the handle portion.
Figure 8B:
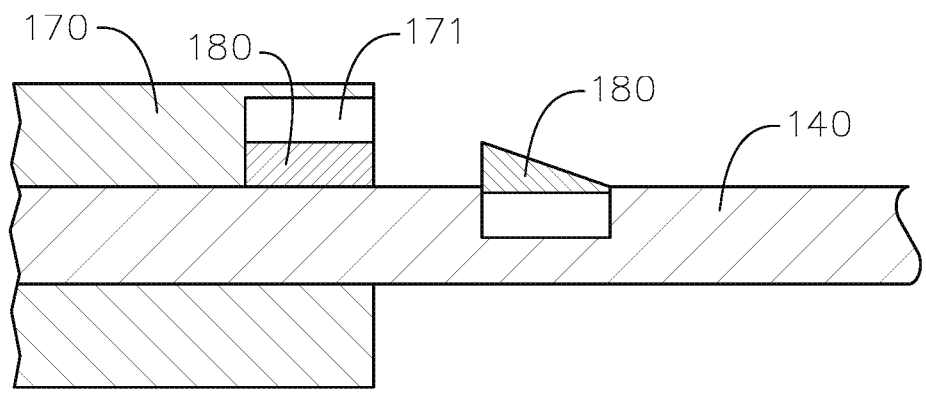
FIG. 8B is a partial view of an intermediate member showing a stop mechanism similar to that shown in FIG. 8A in an expanded state.

FIGS. 8A and 8B illustrate yet another alternative embodiment wherein stop 180 is both disposed on the intermediate member 140 and in handle portion 170. FIG. 8A illustrates stop mechanism 180 in an unexpanded state and FIG. 8B illustrates stop mechanism 180 in an expanded state both within handle 170 and on intermediate member 140.

Alternatively, the stop may be included on the handle portion 170 that prevents proximal movement beyond the point shown in FIG. 3.

The tubular members 120, 140, and 160 may also have a surface treatment and/or coating on their inner surface, outer surface or portions thereof. A coating need not be applied to all of the tubular members 120, 140, 160, and individual members may be coated, uncoated, partially coated, and the like. Useful coating materials may include any suitable biocompatible coating. Non-limiting examples of suitable coatings include, but are not limited to, polytetrafluoroethylene, silicone, hydrophilic materials, hydrogels, and the like. Useful hydrophilic coating materials include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth)acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly(vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth) acrylates; polyacrylic acids; polyacrylamides; polyethylene maleic anhydride, combinations and copolymers thereof, and the like. Additional details of suitable coating materials and methods of coating medical devices with the same among other features may be found in U.S. Pat. Nos. 6,447,835 and 6,890,348, the contents of which are incorporated herein by reference. Such coatings and/or surface treatment can be desirably disposed on the inside or a portion thereof of the external member 160 to aid, if desired, in loading and/or deploying of the stent.

The stent basket 200 may have a truncated-conical shape, being smaller at its proximal end, i.e., outwardly diverging in a distal direction from its proximal engaging end. The stent basket 200 may be a thin film which can collapse such that the stent basket 200 may be slidably contained within the distal end of the external member 160. Alternatively, the stent basket 200 may include a radially distensible member which can be collapsible such that the stent basket 200 can be slidably contained within the external member 160. For instance, the stent basket may be a porous tube, a flexible tube, or any other configurable tube. In some embodiments, the stent basket 200 may be a polymeric member 200. The stent basket 200 may include, in part or substantially, braided filaments 206. The braided filaments 206 may include polymeric filaments, metallic filaments and any other suitable filaments. Alternatively, the braided filaments may be contained within a thin polymeric film.

The stop mechanism can be formed from any of a variety of flexible materials including polymer materials, flexible metals and shape memory metals, and may be the same as or different than the intermediate elongate tubular member to which it is attached.

The stop mechanism is suitably integrated with the intermediate elongate tubular member using any suitable means known in the art such as by overmolding or applying heat to the interface once the stop mechanism is disposed on the intermediate elongate tubular member such as by welding or applying a laser.

Examples of flexible metals for forming the stop mechanism include, but are not limited to, stainless steel, aluminum and copper, for example.

Examples of polymer materials suitable for forming the stop mechanism include, but are not limited to, polyurethanes, polycarbonate and polyesters, for example. Elastomeric polymer materials being preferred.

Examples of shape memory metals suitable for forming the stop mechanism include, but are not limited to, copper-zinc-aluminium-nickel, copper-aluminium-nickel, and nickel-titanium (NiTi) alloys, and can be formed from alloying zinc, copper, gold and iron. Nickel-titanium is a preferred shape memory metal.

Monofilaments available in a variety of polymeric materials including nylon, polyethylene (UHMW), liquid crystal polymers, aramids such as para-aramid, etc. can also be employed herein such as for making a braided stop. Flexible metals and shape memory metals can also be employed in making a web or braid.

The device according to the invention is particularly suited for the loading and delivery of stents and stent/grafts.

These stents and stent/grafts find utility for vascular and non-vascular application. Non-limiting examples include, but are not limited to, the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

A particular example of a non-vascular application is for maintaining esophageal luminal patency in esophageal structures and occlusions of the concurrent esophageal fistulas.

Examples of esophageal stents which can be employed herein include, but are not limited to, the Polyflex® Esophageal Stent, a polyester silicone-covered stent, the WallFlex® stent, WallStent®, and the Ultraflex® stent which is a polyurethane covered Nitinol stent, all commercially available from Boston Scientific/Microvasive, in Natick, Mass.

Stents sold under these tradenames and available from Boston Scientific are also available for use in the tracheobronchial system, the biliary tract, the duodenum and the colon, for example, and can also be used with these loading and delivery systems.

Most particularly, the stents employed herein are self-expanding stents in all forms including, but not limited to, woven, knitted, braided, twisted, knotted, laser cut, welded, etc.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The invention claimed is:

1. A stent loading and delivery system, the delivery system comprising:
    an inner elongate tubular member having a proximal end and a distal end;
    an intermediate elongate tubular member having a proximal end and a distal end, the intermediate elongate tubular member surrounding the inner elongate tubular member and longitudinally slidable relative to the inner elongate tubular member;
    an outer elongate tubular member having a proximal end and a distal end, the outer elongate tubular member surrounding the intermediate elongate tubular member and longitudinally slidable relative to both the inner elongate tubular member and the intermediate elongate tubular member; the proximal end of the outer elongate tubular member movable distally relative to the intermediate elongate tubular member from a first proximal position to a distal position, and then movable proximally relative to the intermediate elongate tubular member from the distal position to a second proximal position, the second proximal position located distal of the first proximal position; and
    a stop disposed on the intermediate elongate tubular member; the stop movable between a first configuration when the proximal end of the outer elongate tubular member is in the first proximal position to a second configuration when the proximal end of the outer elongate tubular member is moved to the distal position, and wherein the stop prevents movement of the proximal end of the outer tubular member back to the first proximal position from the distal position.

2. The stent loading and delivery system of claim 1, wherein the first configuration of the stop is an unexpanded state and the second configuration of the stop is an expanded state.

3. The stent loading and delivery system of claim 1, wherein the inner elongate tubular member comprises a proximal handle at the proximal end of the inner elongate tubular member, the intermediate elongate tubular member comprises an intermediate handle at the proximal end of the intermediate elongate tubular member, and the outer elongate tubular member comprises a distal handle at the proximal end of the outer elongate tubular member, wherein the outer elongate tubular member overlies the stop in the first proximal position.

4. The stent loading and delivery system of claim 3, wherein the distal handle is located distal of the stop in the second proximal position.

5. The stent loading and delivery system of claim 1, wherein the stop permanently prevents the proximal end of the outer elongate tubular member from moving in a proximal direction to the first proximal position after the proximal end of the outer elongate tubular member is moved distally to the distal position.

6. A stent loading and delivery system, the delivery system comprising:
    an inner elongate tubular member having a proximal end and a distal end;
    an intermediate elongate tubular member having a proximal end and a distal end, the intermediate elongate tubular member surrounding the inner elongate tubular member and longitudinally slidable relative to the inner elongate tubular member;
    an outer elongate tubular member having a proximal end and a distal end, the outer elongate tubular member surrounding the intermediate elongate tubular member and longitudinally slidable relative to both the inner elongate tubular member and the intermediate elongate tubular member; the proximal end of the outer elongate tubular member movable distally relative to the intermediate elongate tubular member from a first proximal position to a distal position, and then movable proximally relative to the intermediate elongate tubular member from the distal position to a second proximal position, the second proximal position located distal of the first proximal position;
    a stop disposed on the intermediate elongate tubular member; the stop movable between a first configuration when the proximal end of the outer elongate tubular member is in the first proximal position to a second configuration when the proximal end of the outer elongate tubular member is moved to the distal position, and wherein the stop prevents movement of the proximal end of the outer tubular member back to the first proximal position from the distal position; and a stent loading basket secured to a distal end of the intermediate elongate tubular member and movable therewith.

7. The stent loading and delivery system of claim 6, wherein the stent loading basket extends distally of the distal end of the outer elongate tubular member when the proximal end of the outer elongate tubular member is at the first proximal position.

8. The stent loading and delivery system of claim 7, wherein the distal end of the outer elongate tubular member extends distally of the stent loading basket when the proximal end of the outer elongate tubular member is at the second proximal position.

9. The stent loading and delivery system of claim 6, wherein the stent loading basket is in a radially expanded configuration when the proximal end of the outer elongate tubular member is at the first proximal position.

10. The stent loading and delivery system of claim 9, wherein the stent loading basket is radially constrained by the outer elongate tubular member into a compressed configuration when the proximal end of the outer elongate tubular member is at the second proximal position.

11. The stent loading and delivery system of claim 6, wherein the stent loading basket is configured to surround a proximal end of a stent to load the stent onto the inner elongate tubular member when the proximal end of the outer elongate tubular member is at the first proximal position.

12. The stent loading and delivery system of claim 11, wherein the stent loading basket is prevented from surrounding a proximal end of a stent when the proximal end of the outer elongate tubular member is at the second proximal position.

13. The stent loading and delivery system of claim 6, further comprising an expandable stent having an unconstrained state and a constrained state and having a proximal end and a distal end, wherein the proximal end of the stent is disposed within the stent loading basket.

14. The stent loading and delivery system of claim 13, wherein when the proximal end of the outer elongate tubular member is in the distal position the stent is in the constrained state within the distal end of the external elongate tubular member with the stent loading basket surrounding the proximal end of the stent.

15. The stent loading and delivery system of claim 14, wherein when the proximal end of the outer elongate tubular member is in the distal position and the stop is in the second configuration, the stent is distal of the outer elongate tubular member in the unconstrained state and the stent loading basket is within the outer elongate tubular member.

16. A stent loading and delivery system, the delivery system comprising:
an inner elongate tubular member having a distal end and a proximal handle at a proximal end thereof;
an intermediate elongate tubular member having a distal end and intermediate handle at a proximal end thereof, the intermediate elongate tubular member surrounding the inner elongate tubular member and longitudinally slidable relative to the inner elongate tubular member;
an outer elongate tubular member having a distal end and a distal handle at a distal end thereof, the outer elongate tubular member surrounding the intermediate elongate tubular member and longitudinally slidable relative to both the inner elongate tubular member and the intermediate elongate tubular member; the distal handle of the outer elongate tubular member movable distally relative to the intermediate elongate tubular member from a first proximal position to a distal position, and then movable proximally relative to the intermediate elongate tubular member from the distal position to a second proximal position, the second proximal position located distal of the first proximal position; and
a stop disposed on the intermediate elongate tubular member; the stop movable between a first configuration when the distal handle is in the first proximal position to a second configuration when the distal handle is moved to the distal position, and wherein the stop prevents movement of the distal handle back to the first proximal position from the distal position.

17. The stent loading and delivery system of claim 16, wherein the first configuration of the stop is an unexpanded state and the second configuration of the stop is an expanded state.

18. The stent loading and delivery system of claim 16, wherein the distal handle is located proximal of the stop in the first proximal position, and the distal handle is located distal of the stop in the second proximal position.

19. The stent loading and delivery system of claim 16, further comprising a stent loading basket secured to a distal end of the intermediate elongate tubular member and movable therewith.

20. The stent loading and delivery system of claim 19, wherein the stent loading basket extends distally of the distal end of the outer elongate tubular member when the distal handle is at the first proximal position, and wherein the distal end of the outer elongate tubular member extends distally of the stent loading basket when the distal handle is at the second proximal position.

* * * * *